(12) United States Patent
Kim et al.

(10) Patent No.: US 11,690,888 B2
(45) Date of Patent: Jul. 4, 2023

(54) COMPOSITION FOR PREVENTING OR TREATING MENOPAUSAL SYNDROME, CONTAINING MEDICINAL HERB EXTRACT AS ACTIVE INGREDIENT

(71) Applicants: DONGGUK UNIVERSITY WISE CAMPUS INDUSTRY-ACADEMY COOPERATION FOUNDATION, Gyeongsangbuk-do (KR); KOREA PHARMA CO., LTD., Gyeonggi-do (KR)

(72) Inventors: Dong Il Kim, Gyeonggi-do (KR); Song Hee Jeon, Jeollanam-do (KR); Seung Hee Han, Gyeonggi-do (KR); Kwang Suk Lee, Gyeonggi-do (KR)

(73) Assignees: DONGGUK UNIVERSITY WISE CAMPUS INDUSTRY-ACADEMY COOPERATION FOUNDATION, Gyeongsangbuk-do (KR); KOREA PHARMA CO., LTD., Gyeonggi-do (KR)

( * ) Notice: Subject to any disclaimer, the term of this patent is extended or adjusted under 35 U.S.C. 154(b) by 0 days.

(21) Appl. No.: 16/627,165

(22) PCT Filed: Jun. 7, 2018

(86) PCT No.: PCT/KR2018/006437
§ 371 (c)(1),
(2) Date: Dec. 27, 2019

(87) PCT Pub. No.: WO2019/004626
PCT Pub. Date: Jan. 3, 2019

(65) Prior Publication Data
US 2020/0138889 A1    May 7, 2020

(30) Foreign Application Priority Data
Jun. 30, 2017 (KR) ........................ 10-2017-0083761

(51) Int. Cl.
*A61K 36/43* (2006.01)
*A23L 33/105* (2016.01)
*A61K 36/35* (2006.01)
*A61K 36/754* (2006.01)

(52) U.S. Cl.
CPC ............ *A61K 36/43* (2013.01); *A23L 33/105* (2016.08); *A61K 36/35* (2013.01); *A61K 36/754* (2013.01); *A61K 2236/333* (2013.01)

(58) Field of Classification Search
CPC .............................. A61K 36/43; A61K 36/754
See application file for complete search history.

(56) References Cited

FOREIGN PATENT DOCUMENTS

| JP | 2005-298450 | 10/2005 | |
|---|---|---|---|
| KR | 10-0382040 | 4/2003 | |
| KR | 10-2013-0059532 | 6/2013 | |
| KR | 10-2013-0113810 | 10/2013 | |
| KR | 101333090 B1 * | 11/2013 | |
| KR | 10-2017-0055614 | 5/2017 | |
| KR | 10-2017-0064986 | 6/2017 | |
| WO | WO-2017095011 A1 * | 6/2017 | ........... A61K 36/754 |

OTHER PUBLICATIONS

WO-2017095011-A1 description translated (Year: 2017).*
KR-101333090-B1 description translated (Year: 2013).*
Cheung-Lam (Studies on the uterotonic alkaloids of Fructus Evodiae, Department of Biochemistry, The Chinese University of Hong Kong, May 1979) (Year: 1979).*
Kim et al., "Effects of Cuscutae Semen Extract on Prevention of Osteoporosis in Ovariectomized Rats", The Journal of Oriental Obstetrics & Gynecology, 25(4): 001-011 (2012)—Abstract.
Liu et al., "The osteoprotective effect of Radix Dipsaci extract in ovariectomized rats", Journal of Ethnopharmacology, 123: 74-81 (2009).
International Search Report, dated Sep. 20, 2018 in corresponding International Patent Application No. PCT/KR2018/006437.

* cited by examiner

*Primary Examiner* — Susan Hoffman
*Assistant Examiner* — Jacob A Boeckelman
(74) *Attorney, Agent, or Firm* — Wenderoth, Lind & Ponack, L.L.P.

(57) ABSTRACT

The present invention relates to a composition for preventing or treating menopausal syndrome, containing a medicinal herb extract as an active ingredient. The composition has effects of alleviating heart function deterioration and depression, which are caused by menopause, and has biostability, thereby being usable as a composition for preventing or treating female menopausal syndrome.

4 Claims, 8 Drawing Sheets

COMPOSITION FOR PREVENTING OR TREATING MENOPAUSAL SYNDROME, CONTAINING MEDICINAL HERB EXTRACT AS ACTIVE INGREDIENT

TECHNICAL FIELD

The present invention relates to a composition for preventing or treating menopausal syndrome, containing a medicinal herb extract as an active ingredient.

BACKGROUND ART

Menopause is an inevitable phenomenon that occurs in all women, but the deficiency of female hormones caused by menopause acts as an important factor in inducing physical and mental illness over a long period of time. Representative examples of acute symptoms due to menopause include vasomotor symptoms such as febrile flushing and sweating, mental and emotional symptoms such as depression, anxiety, nerve prevalence and insomnia, and the like. Further, chronic symptoms are symptoms that occur several years after menopause occurs, and include genitourinary symptoms such as anorgasmy, atrophic vaginitis, and urethritis, atherosclerotic circulatory disorders, osteoporosis, and the like.

For the most commonly used hormone replacement therapy for the treatment of climacteric and postmenopausal symptoms, the US Women's Health Initiative (WHI) in 2002 announced that this therapy showed a tendency to increase the risk of developing a disease such as breast cancer, coronary artery disease, and stroke. Accordingly, since serious side effects may be caused by female hormone treatment even in Korea, hormone therapy is recommended to be individually prescribed and used at a low dose for a short period of time in consideration of the risks and benefits of each individual, and the treatment purpose and risk change over the passage of time, so that it is recognized that a periodic re-evaluation is required.

In Korea, various symptoms after climacterium and menopause have been traditionally treated by treatment methods such as acupuncture and Oriental herbal medicine, and recently, due to side effects of hormone replacement therapy, more women have tried to solve clinical problems after menopause by Korean traditional medical treatment methods.

Meanwhile, cuscutae semen is the seed of *Cuscuta chinensis* Lamark, and is known as a medicine which usually protects the liver and the kidneys, brightens the eyes, helps the yang-gi (positive energy), and strengthens kidney functions. Evodiae fructus is the fruit of *Evodia rutaecarpa* Bentham var. *officinalis* Huang, *Evodia rutaecarpa* Bentham var. *bodinieri* Huang, or the like, contains volatile essential oil, and is known to be effective for stomachaches that occur when the digestion is weak and the whole body is cold, regulate stomach functions, and enhance digestibility. *Dipsaci radix* is the root of *Dipsacus asper* Wall, and is known to have effects of protecting the liver and the kidneys and strengthening the muscle and the bones.

As an animal model for studying menopause, ovariectomized (OVX) rats or mice from which the ovaries have been excised by surgical methods have been used until recently, but since almost 90% of menopausal women have ovaries, the OVX model has limitations. Recently, a menopausal animal model induced by VCD has been developed as a model to overcome these limitations, and the VCD-induced menopausal model selectively promotes the natural disappearance of primordial follicles and primary follicles without affecting other tissues of the uterus, and thus is very similar to the human menopausal process, and also has an advantage in that it is possible to observe both the peri-menopausal and post-menopausal processes unlike the OVX model that shows only the post-menopausal process.

Thus, as a result of efforts to develop a new drug that is highly effective in preventing or treating female menopausal syndrome and has fewer side effects, the present inventors confirmed that a mixed extract of cuscutae semen, *Evodiae fructus*, and *Dipsaci radix* has effects of alleviating heart function deterioration and depression, which are caused by menopause in a VCD menopausal animal model, thereby completing the present invention.

DETAILED DESCRIPTION OF THE INVENTION

Technical Problem

One object of the present invention is to provide a composition for preventing or treating female menopausal syndrome, containing a mixed extract of cuscutae semen, *Evodiae fructus*, and *Dipsaci radix* as an active ingredient.

Technical Solution

An aspect of the present invention provides a composition for preventing or treating female menopausal syndrome, containing a mixed extract of cuscutae semen, *Evodiae fructus*, and *Dipsaci radix* as an active ingredient.

According to an exemplary embodiment of the present invention, the mixed extract may be an extract obtained by extracting a mixed powder of cuscutae semen, *Evodiae fructus*, and *Dipsaci radix* with any one or more solvents selected from the group consisting of water, an alcohol having 1 to 4 carbon atoms, and a mixed solvent thereof.

According to an exemplary embodiment of the present invention, the cuscutae semen, *Evodiae fructus*, and *Dipsaci radix* may be included at a ratio of 15 to 60 wt %:5 to 50 wt %:15 to 60 wt %, respectively, and may be included preferably at a ratio of 20 to 30 wt %:10 to 15 wt %:20 to 30 wt %, respectively.

According to an exemplary embodiment of the present invention, the menopausal syndrome may be caused by a decrease in estrogen secretion.

According to an exemplary embodiment of the present invention, the menopausal syndrome may be selected from the group consisting of arteriosclerotic cardiovascular disease, tachycardia, facial flushing, palpitation, sweating, osteoporosis, depression, urinary incontinence, dysuria, acute cystitis, recurrent urinary tract inflammation, and alopecia.

According to an exemplary embodiment of the present invention, the composition may be a pharmaceutical composition.

According to an exemplary embodiment of the present invention, the composition may be a food composition.

Advantageous Effects

According to a composition for preventing or treating menopausal syndrome, containing a medicinal herb extract as an active ingredient according to the present invention, the composition has effects of alleviating heart function deterioration and depression, which are caused by menopause, and has biostability, thereby being usable as a composition for preventing or treating female menopausal syndrome.

BEST MODE

Figure 1:
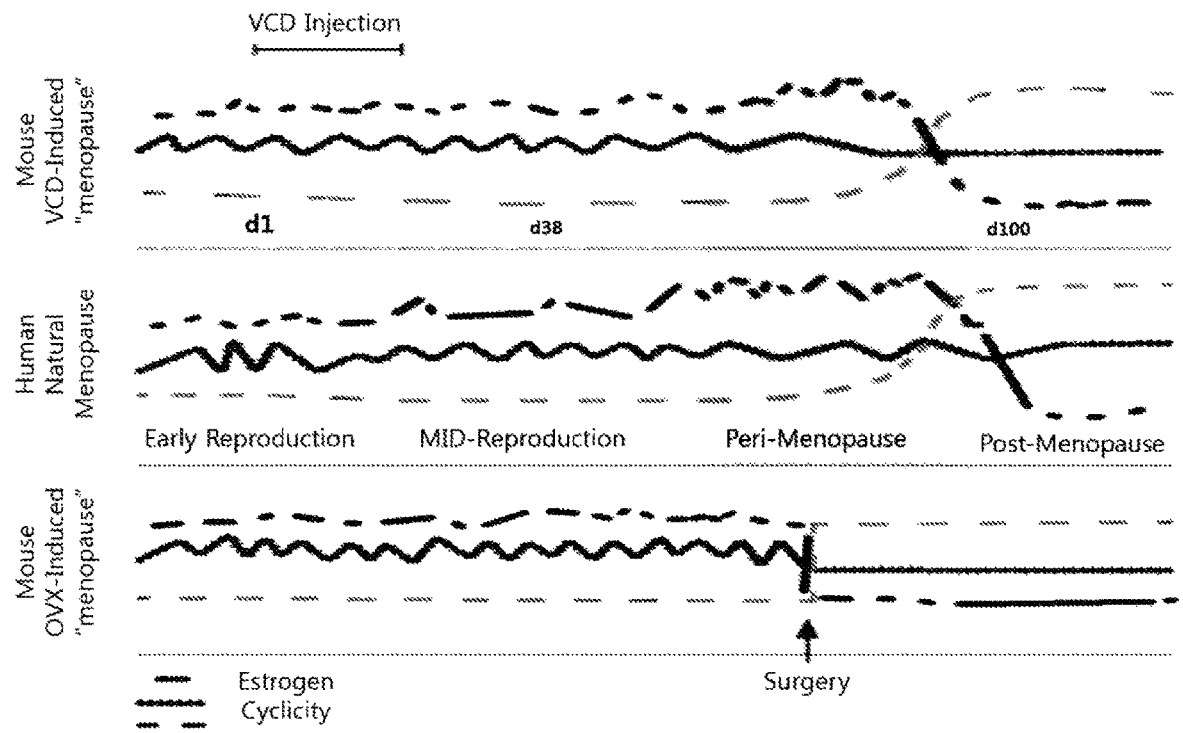
FIG. 1 is a view illustrating comparison of menopausal processes of a VCD menopausal animal model, human menopause, and an OVX menopausal animal model.

An aspect of the present invention provides a composition for preventing or treating female menopausal syndrome, containing a mixed extract of cuscutae semen, *Evodiae fructus*, and *Dipsaci radix* as an active ingredient.

Menopausal syndrome collectively refers to a disorder experienced in relation to a decrease in estrogen secretion in menopausal women, and may include cardiovascular disorders such as arteriosclerotic cardiovascular disease occurring after menopause, neurovascular abnormalities such as tachycardia, facial flushing, palpitation, and sweating, locomotor abnormalities such as osteoporosis, psychoneurological abnormalities such as depression, urinary incontinence, dysuria, acute cystitis, recurrent urinary tract inflammation, changes in skin tissue, alopecia, and the like.

The composition of the present invention has effects of alleviating heart function deterioration and depression, which are caused by menopause, and has biostability, thereby being used in treating various disorders occurring after menopause.

The composition according to the present invention may be obtained as follows. Impurities are removed by washing cuscutae semen, *Evodiae fructus*, and *Dipsaci radix* with water, and then dried in the shade and ground. *Cuscutae semen*, *Evodiae fructus*, and *Dipsaci radix* which are cultivated or commercially available may be used without limitation. A suitable amount of solvent is added to the powder of ground cuscutae semen, *Evodiae fructus*, and *Dipsaci radix* to commercially immerse cuscutae semen, *Evodiae fructus*, and *Dipsaci radix*. A mixed powder of cuscutae semen, *Evodiae fructus*, and *Dipsaci radix* may be extracted using a typical extraction solvent, may be extracted using preferably (a) an hydrous or water-containing lower alcohol having 1 to 4 carbon atoms (for example: methanol, ethanol, propanol, butanol, normal-propanol, iso-propanol, normal-butanol, and the like), (b) a mixed solvent of the lower alcohol and water, (c) acetone, (d) ethyl acetate, (e) chloroform, (f) 1,3-butylene glycol, (g) hexane, (h) diethyl ether, (i) butyl acetate, or (j) water, and may be extracted using most preferably water or ethanol. During extraction, cuscutae semen, *Evodiae fructus*, and *Dipsaci radix* may be impregnated at room temperature or warmed. A final extract may be obtained by filtering the extracted liquid and concentrating the extracted liquid.

According to an exemplary embodiment of the present invention, the mixed extract may be an extract obtained by extracting a mixed powder of cuscutae semen, *Evodiae fructus*, and *Dipsaci radix* with any one or more solvents selected from the group consisting of water, an alcohol having 1 to 4 carbon atoms, and a mixed solvent thereof.

According to an exemplary embodiment of the present invention, the cuscutae semen, *Evodiae fructus*, and *Dipsaci radix* may be included at a ratio of 15 to 60 wt %:5 to 50 wt %:15 to 60 wt %, respectively, and may be included preferably at a ratio of 20 to 30 wt %:10 to 15 wt %:20 to 30 wt %, respectively.

According to an exemplary embodiment of the present invention, the menopausal syndrome may be caused by a decrease in estrogen secretion.

According to an exemplary embodiment of the present invention, the menopausal syndrome may be selected from the group consisting of arteriosclerotic cardiovascular disease, tachycardia, facial flushing, palpitation, sweating, osteoporosis, depression, urinary incontinence, dysuria, urinary retention, recurrent urinary tract inflammation, and alopecia.

According to an exemplary embodiment of the present invention, the composition may be a pharmaceutical composition.

When the composition of the present invention is prepared as a pharmaceutical composition, the pharmaceutical composition of the present invention contains a pharmaceutically acceptable carrier. A pharmaceutically acceptable carrier contained in the pharmaceutical composition of the present invention is typically used during formulation, and includes lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like, but is not limited thereto. The pharmaceutical composition of the present invention may additionally contain a lubricant, a wetting agent, a sweetening agent, a flavoring agent, an emulsifier, a suspending agent, a preservative, and the like, in addition to the aforementioned ingredients. Suitable pharmaceutically acceptable carriers and formulations are described in detail in Remington's Pharmaceutical Sciences (22th ed., 2013).

The pharmaceutical composition of the present invention may be administered orally or parenterally, and is preferably applied in an oral administration mode. A suitable dose of the pharmaceutical composition of the present invention may vary depending on factors, such as formulation method, administration method, age, body weight, sex or disease condition of the patient, diet, administration time, administration route, elimination rate and response sensitivity. A preferred dose of the pharmaceutical composition of the present invention is within a range of 0.001 to 1,000 mg/kg based on an adult.

The pharmaceutical composition of the present invention may be prepared in the form of a unit-dose or by being contained in a multi-dose container by being formulated using a pharmaceutically acceptable carrier and/or excipient according to a method that can be readily implemented by a person with ordinary skill in the art to which the present invention pertains. In this case, a dosage form may also be in the form of a solution in an oil or aqueous medium, a suspension, a syrup, or an emulsion or in the form of an extract, an acida, a powder, a granule, a tablet or a capsule, and the pharmaceutical composition of the present invention may additionally contain a dispersant or a stabilizer.

According to an exemplary embodiment of the present invention, the composition may be a food composition.

When the composition of the present invention is prepared as a food composition, the composition of the present invention may contain not only a mixed extract of cuscutae semen, *Evodiae fructus*, and *Dipsaci radix* as an active ingredient, but also ingredients typically added during the production of food, and may contain, for example, protein, carbohydrate, fat, nutrient, seasoning, and a flavoring agent. As the carbohydrate, it is possible to use a typical sugar such as a monosaccharide (for example, glucose, fructose, and the like), a disaccharide (for example, maltose, sucrose, oligosacchride, and the like) and/or a polysaccharide (for example, dextrin, cyclodextrin, and the like) and/or a sugar alcohol such as xylitol, sorbitol, and erythritol. As the flavoring agent, it is possible to use a natural flavoring agent (thaumatin, stevia extract (for example, Rebaudioside A, glycyrrhizin and the like)) and/or a synthetic flavoring agent (saccharin, aspartame, and the like).

Further, the food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like. These ingredients may be used independently or in combination, and the proportion of these additives may be selected within a range of 0 to about 20 parts by weight per 100 parts by weight of the food composition of the present invention, but is not limited thereto.

The mixed extract of the cuscutae semen, *Evodiae fructus*, and *Dipsaci radix* of the present invention may be prepared as a food composition for preventing or alleviating various menopausal syndromes by methods for preparing a dosage form generally used in the art. For example, the extract may be prepared as a typical health functional food formulation such as a beverage or a pill, and a powder. When the food composition of the present invention is prepared as a drink, the composition may additionally contain citric acid, liquid fructose, sugar, sucrose, acetic acid, malic acid, a fruit juice, a legume extract, a jujube extract, a licorice extract, and the like in addition to the mixed extract of the cuscutae semen, *Evodiae fructus*, and *Dipsaci radix* of the present invention.

Another aspect of the present invention provides a method for treating menopausal syndrome, the method including: administering the mixed extract of the cuscutae semen, *Evodiae fructus*, and *Dipsaci radix* of the present invention to a patient with the menopausal syndrome.

MODE FOR INVENTION

Hereinafter, one or more specific exemplary embodiments will be described in more detail through Examples. However, these Examples are provided only for exemplarily explaining one or more specific exemplary embodiments, and the scope of the present invention is not limited to these Examples.

Example 1: Analysis Method of Effects of Medicinal Herb Mixed Extract on Alleviation of Menopausal Syndrome 1-1: Preparation of Medicinal Herb Mixed Extract by Freeze-Drying Method or Spray-Drying Method Carefully selected cuscutae semen, *Evodiae fructus*, and *Dipsaci radix* were put into an extraction cloth in the weights shown in the following Table 1, primarily extracted by heating the resulting mixture with 16 L of water at 80° C. for 4 hours, and secondarily extracted by heating the mixture again at 80° C. for 4 hours. The extract that was primarily filtered by a 120 mesh filter was secondarily filtered by a 5 μm filter, then transferred to a buffer tank and concentrated to 15 Bx. The concentrated extract is prepared as a final extract by the freeze-drying method or the spray-drying method.

In the case of the freeze-drying method, the extract concentrated to 15 Bx was sterilized at 85° C. for 1 hour, and then freeze-dried for 5 days by freezing the extract, and finally, 198.8 g of an extract was obtained from a total 2 kg of raw materials (yield: 19.8%).

In the case of the spray-drying method, the extract concentrated to 15 Bx was diluted to 12.98 Bx and sterilized at 85° C. for 1 hour, and then the extract was spray-dried under conditions of an inlet temperature of 190° C., an outlet temperature of 90° C., a punching of 10 sec/time, and a flow rate of 1.0 L/hr, and finally, 170.2 g of an extract was obtained from a total 2 kg of raw materials (yield: 17%).

TABLE 1

| Name of herbal medicine | English name | Amount (g) |
| --- | --- | --- |
| Tosaja | cuscutae semen | 800 g |
| Ohsuyu | Evodiae fructus | 400 g |
| Sokdan | Dipsaci radix | 800 g |
| Total amount | | 2000 g |

1-2: Preparation of Medicinal Herb Mixed Extract by Ethanol Extraction Method

Carefully selected cuscutae semen, *Evodiae fructus*, and *Dipsaci radix* were put into an extraction cloth in the weights shown in Table 1, primarily extracted by heating the resulting mixture with 16 L of 30% ethanol at 80° C. for 4 hours, and secondarily extracted by heating the mixture again at 80° C. for 4 hours. The extract that was primarily filtered by a 120 mesh filter was secondarily filtered by a 5 µm filter, then transferred to a buffer tank and concentrated to 15 Bx. The concentrated extract is prepared as a final extract by the freeze-drying method or the spray-drying method.

The subsequent freeze-drying method or spray-drying method is the same as the process of Example 1-1, and in the case of the freeze-drying method, 185.2 g of an extract was obtained from a total of 2 kg of raw materials (yield: 18.5%), and in the case of the spray-drying method, 168.2 g of an extract was obtained from a total of 2 kg of raw materials (yield: 16.8%).

1-3: Design of VCD Menopausal Animal Model 4-week-old C57BL/6 female mice were used, adapted to a breeding environment for 1 week, and then used for the experiment. The experimental group was divided into 5 groups as follows, and each group was treated as follows.

Group 1 (Sham group): Group which was intraperitoneally administered with sesame oil for 17 days, and then fed with a general dietary feed for 15 weeks, Group 2 (VCD group): Group which was fed with a general dietary feed for 15 weeks after VCD menopause was induced by administering sesame oil (2.5 mg/kg) and VCD (160 mg/kg) to the abdominal cavity of mice for 17 days, Group 3 (Low concentration group): Group which was fed with a feed containing the extract (100 mg/kg) in Example 1-1 for 15 weeks after VCD menopause was induced in the same manner as in Group 2, Group 4 (High concentration group): Group which was fed with a feed containing the extract (300 mg/kg) in Example 1-1 for 15 weeks after VCD menopause was induced in the same manner as in Group 2, and Group 5 (Estradiol group): Group which was fed with a feed containing estradiol (2 mg/kg) for 15 weeks after VCD menopause was induced in the same manner as in Group 2.

1-4: Measurement of Body Weight and Feed Intake and Analysis of Food Efficiency Ratio (FER)

The body weight and feed intake were measured every one week, and after the experiment was completed, the food efficiency ratio was analyzed during the experimental period. The food efficiency ratio was calculated by (weight gain/total feed intake)×100 and analyzed.

1-5: Measurement of Weights and Indices of Heart, Ovaries and Uterus

After the experiment was completed, the weights of the heart, ovaries, and weights of each experimental mouse were measured, and the index of each organ was calculated as a percentage of each organ weight to the body weight of the experimental animal.

1-6: Behavioral Experiment (Open Field Test)

The experimental mice were allowed to move freely in a white box of 40 cm×40 cm×40 cm for 10 minutes. Lines were drawn on the bottom of the box at an interval of 10 cm, and a horizontal and vertical 10 cm box was drawn at the center of the box. The movement of the experimental mice was measured with a video camera, and the time in the center and the total traveled distance were analyzed using ANY-maze which is a behavior analysis program.

1-7: Blood Analysis

After the experimental mice were anesthetized with avertin tribromoethanol, blood was collected from the saphenous vein and centrifuged at 2000 g for 15 minutes at 4° C., and the supernatant was carefully separated, and then stored at −80° C. Thereafter, from the serum stored at −80° C., the concentrations of total cholesterol in blood, high-density lipoprotein (HDL), triglyceride (TG), glutamic oxalacetic transaminase (GOT)/glutamic pyruvate transaminase (GPT), and glucose were measured using a commercially available kit.

1-8: Statistical Processing

All analytical data results used SPSS 23 (SPSS Inc., Chicago, Ill., USA), and statistical significance tests were based on the level at $p<0.05$ and expressed as mean±standard error (mean±SE). After one-way analysis of variance (one-way ANOVA), post-validation was performed using the Tukey's multiple comparison test or Dunnett's test for statistical significance between samples.

Example 2: Confirmation of Body Weight, Food Intake, and Food Efficiency Ratio

It was confirmed whether there was a difference in body weight, food intake, and food efficiency ratio between the group that was fed with the feed containing the extract of Example 1-1 and the group that was fed with the feed that did not contain the extract of Example 1-1.

Specifically, each change in body weight, food intake, and food efficiency ratio of 5 experimental groups were analyzed by the method of Example 1-4.

Figure 2:
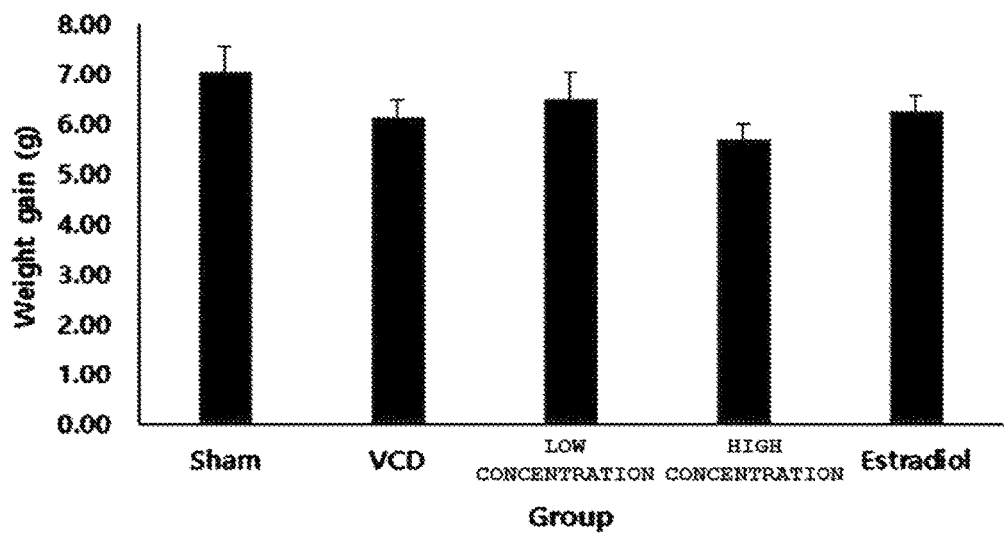
FIG. 2 is a graph illustrating the weight gain of each group that was fed with a general diet and a diet containing the extract of the present invention.
Figure 3:
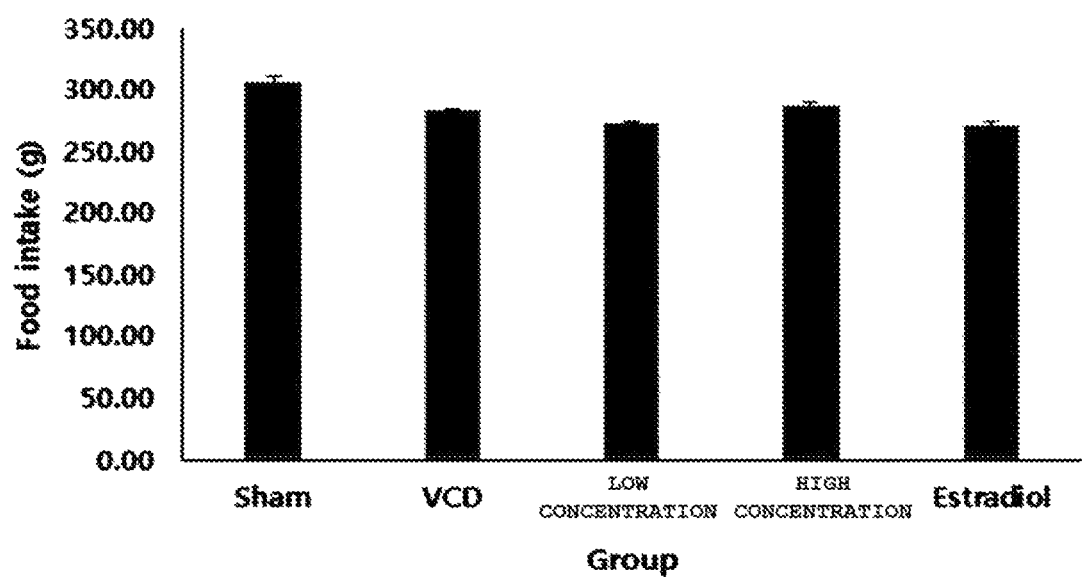
FIG. 3 is a graph illustrating the food intake of each group that was fed with a general diet and a diet containing the extract of the present invention.
Figure 4:
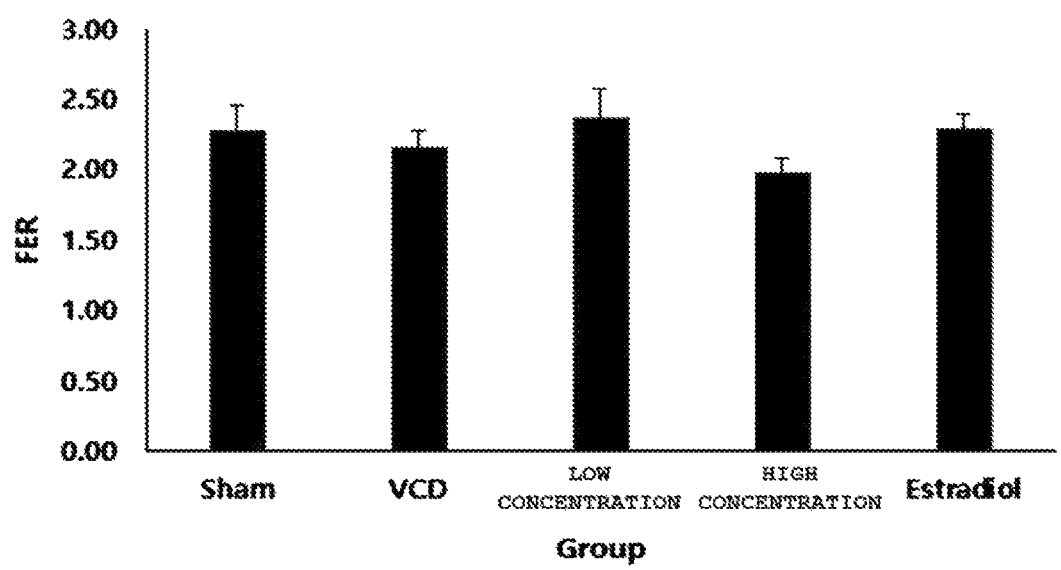
FIG. 4 is a graph illustrating the food efficiency ratio of each group that was fed with a general diet and a diet containing the extract of the present invention.

As a result, the Sham was the highest in weight gain and food intake, and the other groups showed similar tendencies (FIGS. 2 and 3), and the food efficiency ratio was the lowest in the high concentration group, but there was no significance (FIG. 4). Through the results, it was confirmed that the mixed extract of the present invention did not cause a body weight gain after menopause.

Example 3: Confirmation of Normalization of Weights and Indices of Heart, Ovaries and Uterus It was confirmed whether the weights and indices of the organs were restored normally in the group which was fed with the feed containing the extract of Example 1-1.

Specifically, in order to confirm whether uterine atrophy and heart hypertrophy symptoms occurring after menopause were induced, the analysis according to Example 1-5 was performed.

Figure 5:
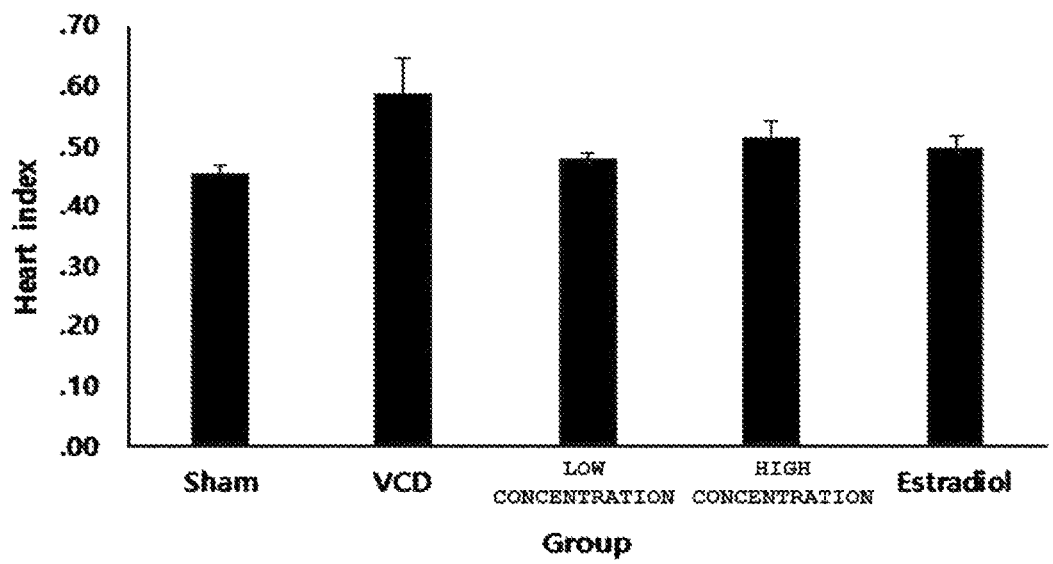
FIG. 5 is a graph illustrating the heart index of each group that was fed with a general diet and a diet containing the extract of the present invention.

As a result, the heart index is the highest in the VCD group, and it could be seen that the disease such as heart hypertrophy after menopause was induced, and it was confirmed that in the case of the low concentration group, the high concentration group, and the Estradiol group, the heart index was restored to the Sham's level (FIG. 5).

Figure 6:
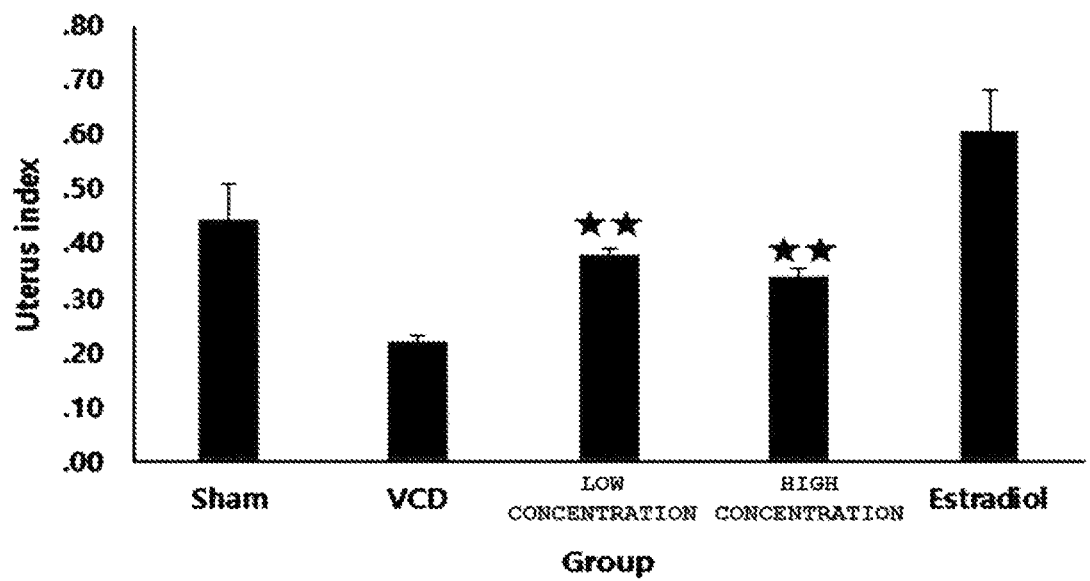
FIG. 6 is a graph illustrating the uterus index of each group that was fed with a general diet and a diet containing the extract of the present invention.
Figure 7:
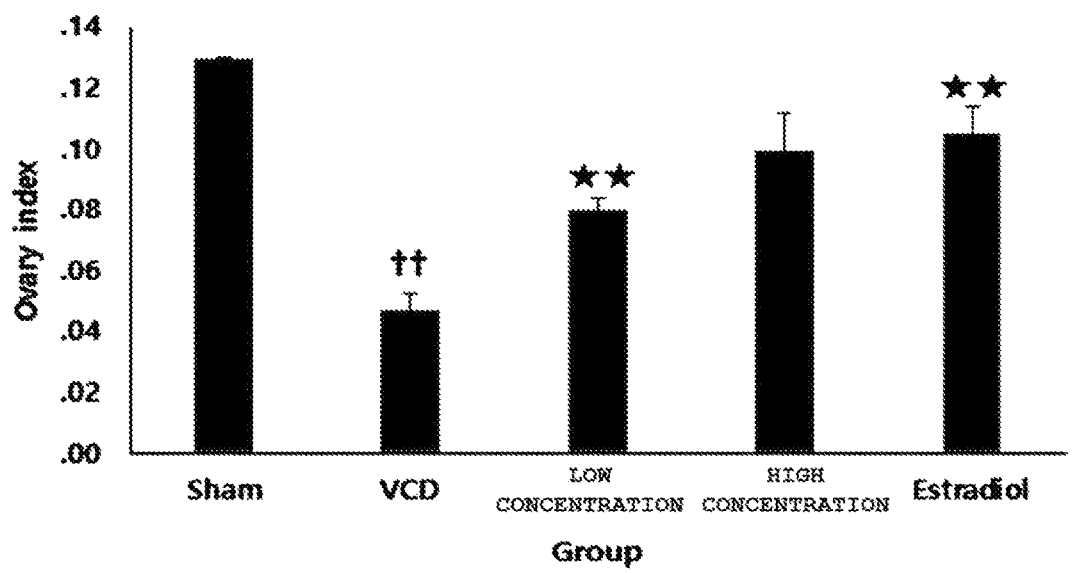
FIG. 7 is a graph illustrating the ovary index of each group that was fed with a general diet and a diet containing the extract of the present invention.

The uterus index was the lowest in the VCD group, but it was confirmed that in the case of the low concentration group and the high concentration group, the uterus index was significantly recovered to the Sham group's level ($p<0.01$) (FIG. 6), and the lowest numerical value was also exhibited in the VCD group ($p<0.01$), but in the low concentration group and the Estradiol group, the ovary index was significantly recovered ($p<0.01$) (FIG. 7).

Example 4: Confirmation of Effects of Alleviating Menopausal Depression Symptoms It was confirmed whether the menopausal depression symptoms were alleviated in the group that was fed with the feed containing the extract of Example 1-1.

Specifically, in order to confirm the efficacy of the mixed extract of the present invention on anxiety and activity deterioration caused by depression after menopause, the analyses according to Examples 1-6 and 1-7 were performed.

Figure 8:
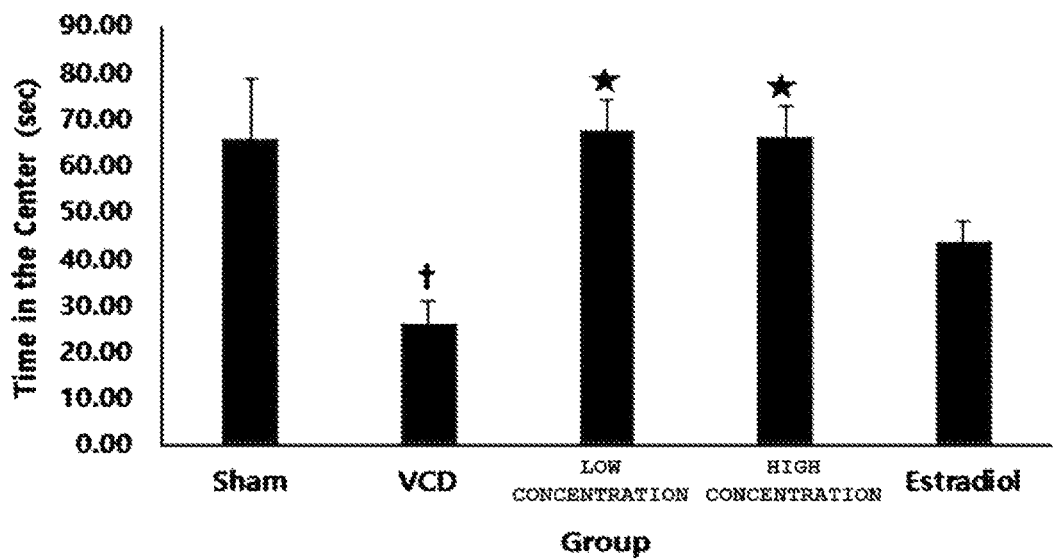
FIG. 8 is a graph illustrating the time spent in the center of a test box for each group that was fed with a general diet and a diet containing the extract of the present invention.
Figure 9:
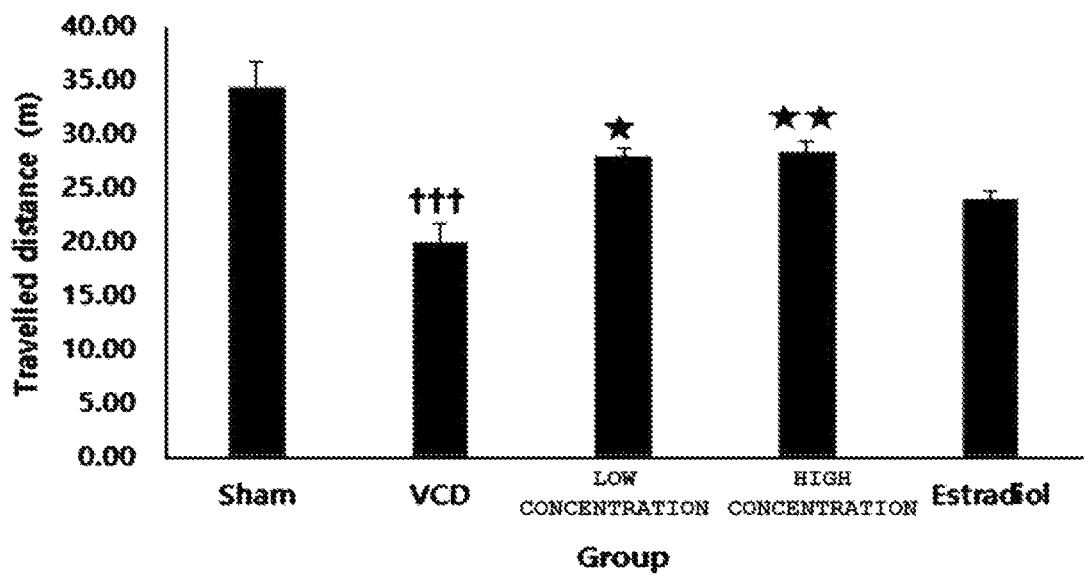
FIG. 9 is a graph illustrating the traveled distance in a test box for each group that was fed with a general diet and a diet containing the extract of the present invention.

As a result, in the case of the VCD group, the time spent in the center of a test box was remarkably reduced compared to the Sham group ($p<0.05$), and in the case of the low concentration group and the high concentration group, the time spent in the center of the test box was significantly recovered to the Sham's level ($p<0.05$) (FIG. 8). The overall traveled distance was also clearly reduced in the VCD group compared to the Sham ($p<0.001$), but was increased significantly in the low concentration group and the high concentration group ($p<0.05$ and $p<0.01$, respectively) (FIG. 9).

Figure 10:
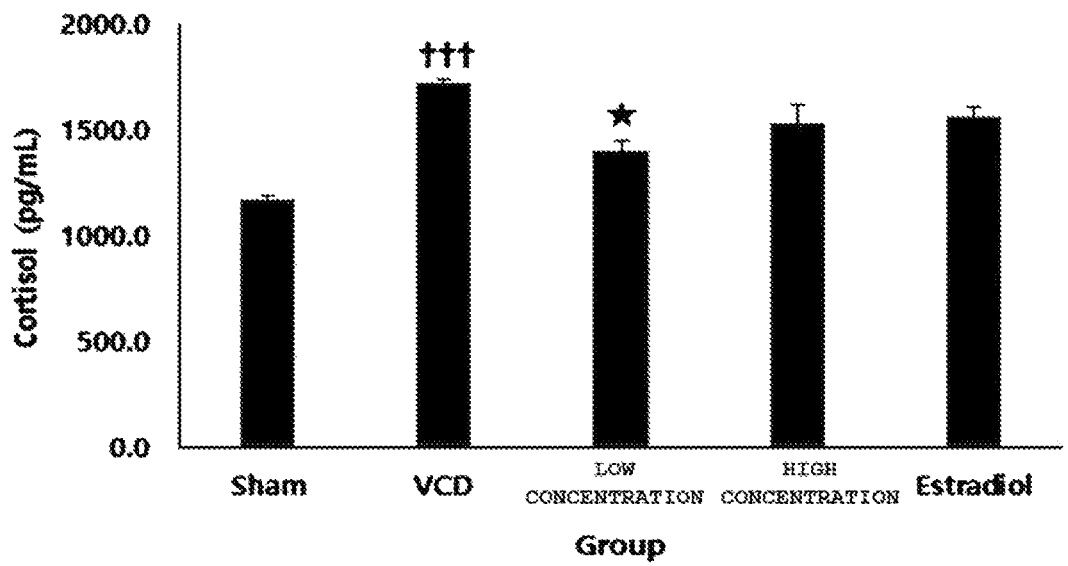
FIG. 10 is a graph illustrating the cortisol value of each group that was fed with a general diet and a diet containing the extract of the present invention.

Further, as a result of measuring the cortisol value in blood, it was confirmed that the cortisol value in blood was rapidly increased in the VCD group ($p<0.001$), but the cortisol value in blood was reduced in all the groups taking the mixed extract of the present invention, and the cortisol value in blood was significantly reduced particularly in the low concentration group ($p<0.05$) (FIG. 10).

Example 5: Confirmation of Effects of Improving Cardiovascular Factors

It was confirmed whether cardiovascular factors were improved in the group which was fed with the feed containing the extract of Example 1-1.

Specifically, in order to confirm the concentrations of total cholesterol, HDL cholesterol, triglyceride (TG), and glucose in blood after menopause, an analysis according to Example 1-7 was performed.

Figure 11:
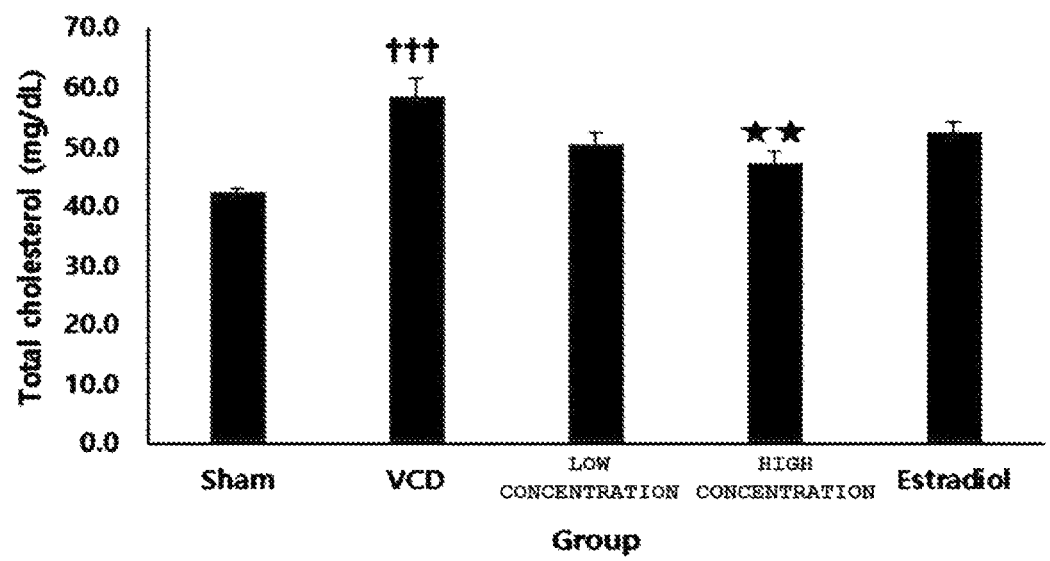
FIG. 11 is a graph illustrating the total cholesterol concentration of each group that was fed with a general diet and a diet containing the extract of the present invention.
Figure 12:
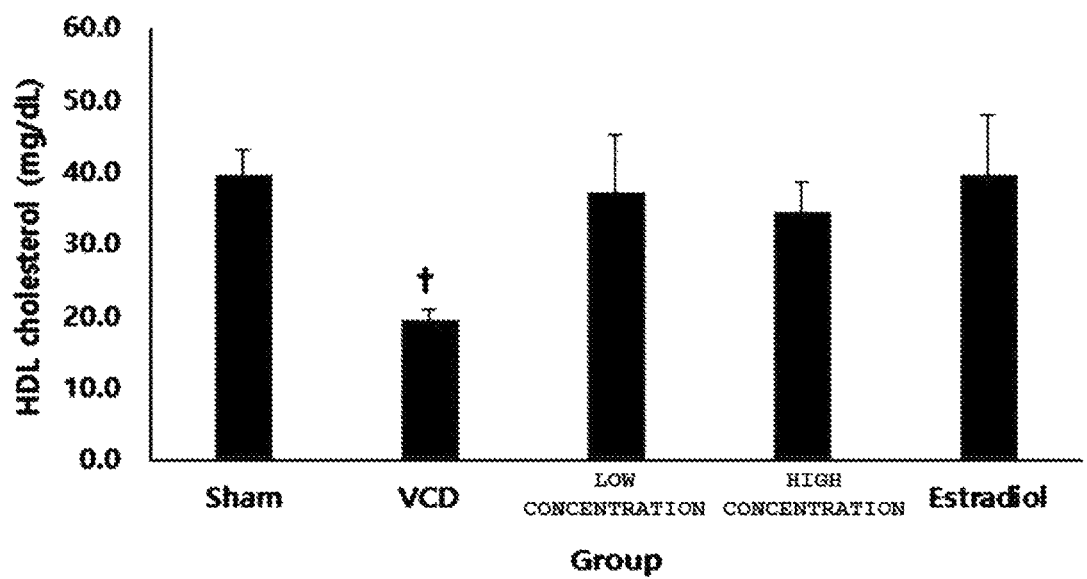
FIG. 12 is a graph illustrating the HDL cholesterol concentration of each group that was fed with a general diet and a diet containing the extract of the present invention.

As a result, in the VCD group, the concentration of total cholesterol was remarkably increased compared to the Sham ($p<0.001$), and in the high concentration group, the concentration of total cholesterol was decreased to the Sham' level ($p<0.01$) (FIG. 11), and in contrast, the HDL cholesterol was significantly decreased in the VCD group ($p<0.05$), but showed a tendency to be recovered in the medicine intake group (FIG. 12).

Figure 13:
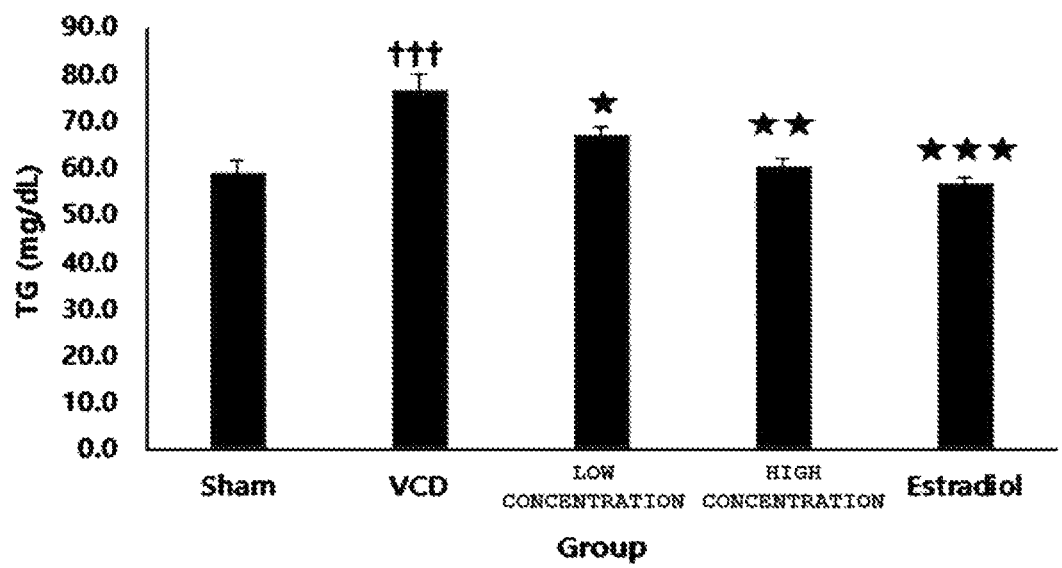
FIG. 13 is a graph illustrating the triglyceride concentration of each group that was fed with a general diet and a diet containing the extract of the present invention.
Figure 14:
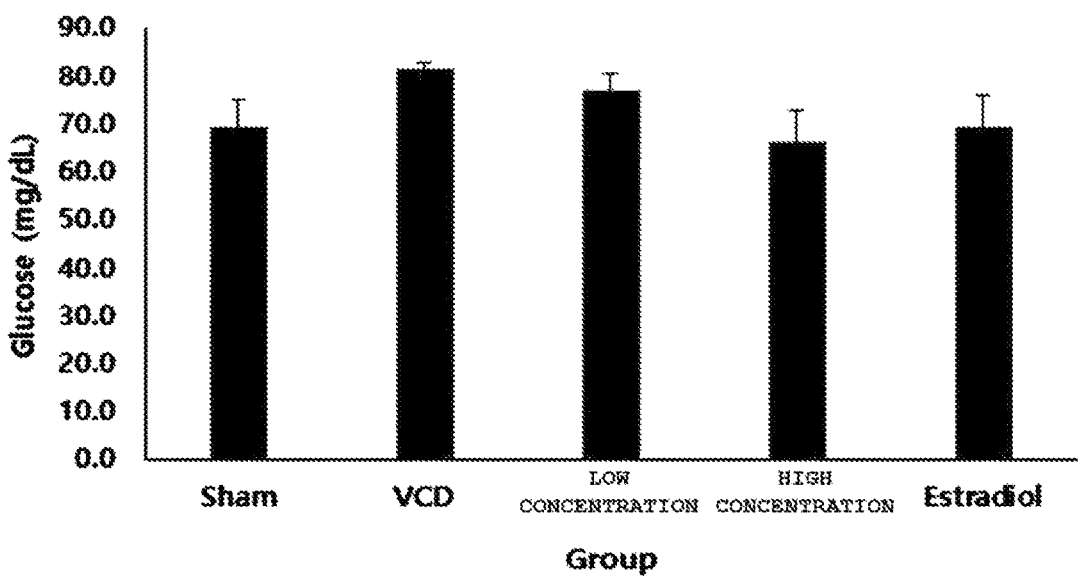
FIG. 14 is a graph illustrating the glucose concentration of each group that was fed with a general diet and a diet containing the extract of the present invention.

In addition, the triglyceride was remarkably increased in the VCD group ($p<0.001$), but was significantly decreased in the low concentration group, the high concentration group, and the Estradioil group ($p<0.05$, $p<0.01$, and $p<0.001$, respectively) (FIG. 13). Each group did not show any significant difference in glucose, but the glucose concentration in the medicine intake group was measured to be lower than that in the VCD group (FIG. 14).

Example 6: Hepatotoxicity Test

It was confirmed whether hepatotoxicity occurred in the group which was fed with the feed containing the extract of Example 1-1.

Specifically, it was analyzed whether hepatotoxicity occurred due to the intake of the mixed extract of the present invention by measuring the value of GOT/GPT in blood according to Example 1-7.

Figure 15:
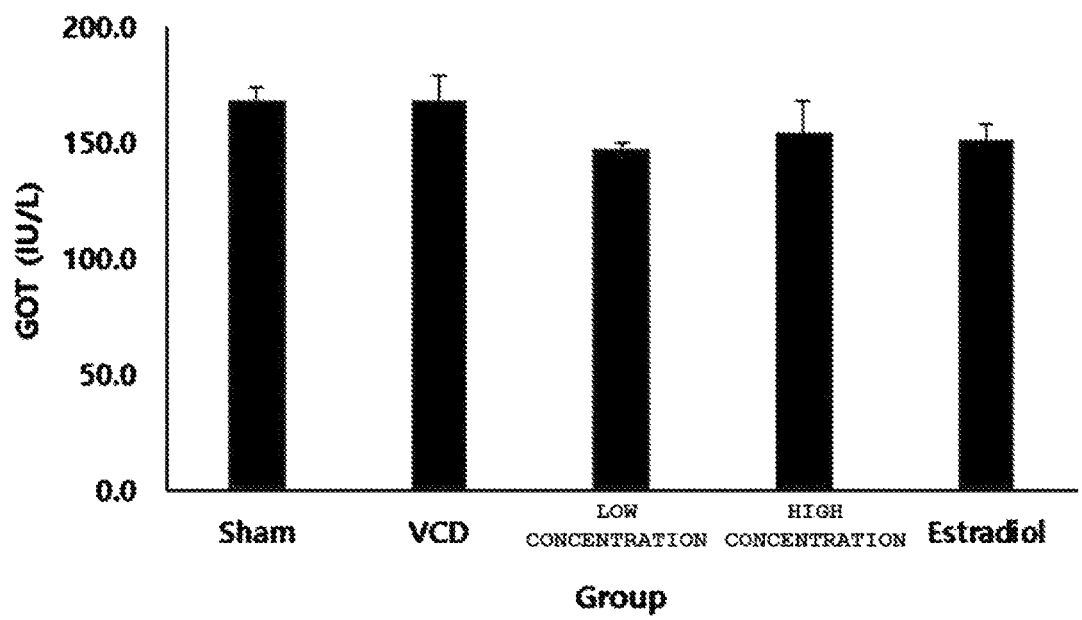
FIG. 15 is a graph illustrating the GOT value of each group that was fed with a general diet and a diet containing the extract of the present invention.
Figure 16:
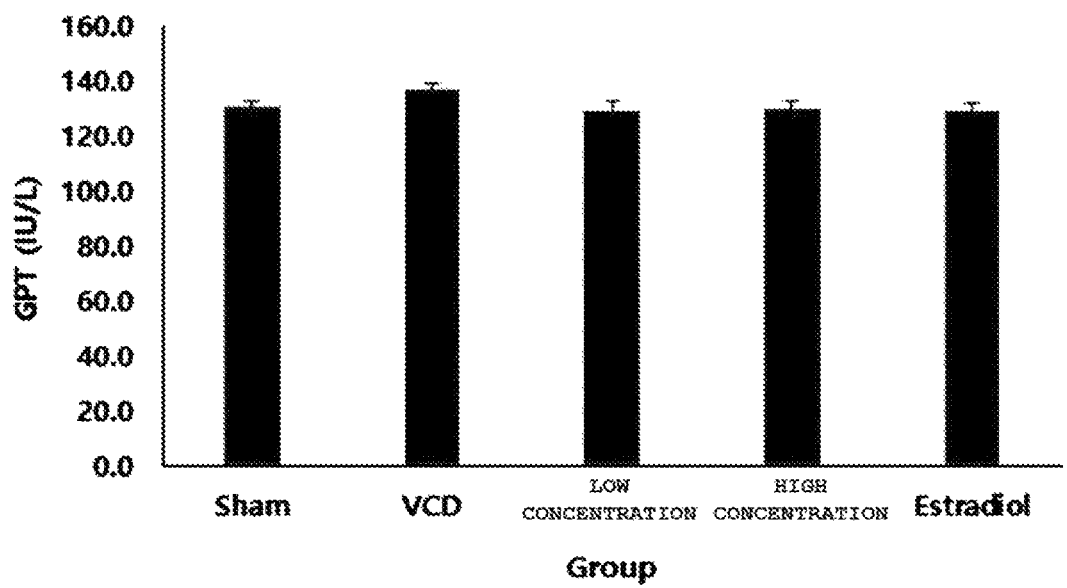
FIG. 16 is a graph illustrating the GPT value of each group that was fed with a general diet and a diet containing the extract of the present invention.

As a result, the GOT/GPT values of all the groups showed a similar trend (FIGS. 15 and 16), confirming that the mixed extract of the present invention had no hepatotoxicity for the experimental animals.

From the foregoing, the present invention has been reviewed mainly based on the preferred examples thereof. A person with ordinary skill in the art to which the present invention pertains will be able to understand that the present invention may be implemented in a modified form without departing from the essential characteristics of the present invention. Therefore, the disclosed examples should be considered not from a restrictive viewpoint, but from an explanatory viewpoint. The scope of the present invention is defined not in the above-described description, but in the claims, and it should be interpreted that all the differences within a range equivalent thereto are included in the present invention.

The invention claimed is:

1. A method for treating menopausal syndrome, the method comprising administering a therapeutically effective amount of a mixed extract consisting of cuscutae semen, *Evodiae fructus*, and *Dipsaci radix* to a patient with the menopausal syndrome,
   wherein the cuscutae semen, *Evodiae fructus*, and *Dipsaci radix* are mixed at a ratio of 15 to 60 wt %:5 to 50 wt %:15 to 60 wt %,
   wherein a total of the cuscutae semen and *Dipsaci radix* is more than 50 wt % of the extract, and
   wherein the patient has ovaries.

2. The method of claim 1, wherein the mixed extract is obtained by extracting a mixed powder of cuscutae semen, *Evodiae fructus*, and *Dipsaci radix* with any one or more solvents selected from the group consisting of water, an alcohol having 1 to 4 carbon atoms, and a mixed solvent thereof.

3. The method of claim 1, wherein the menopausal syndrome is caused by a decrease in estrogen secretion.

4. The method of claim 1, wherein the menopausal syndrome is selected from the group consisting of arteriosclerotic cardiovascular disease, tachycardia, facial flushing, palpitation, sweating, osteoporosis, depression, urinary incontinence, dysuria, acute cystitis, recurrent urinary tract inflammation, and alopecia.

\* \* \* \* \*